United States Patent [19]

Burns

[11] Patent Number: 4,616,649

[45] Date of Patent: Oct. 14, 1986

[54] LANCET

[75] Inventor: James A. Burns, Elizabeth, N.J.

[73] Assignee: Becton, Dickinson and Company, Franklin Lakes, N.J.

[21] Appl. No.: 652,386

[22] Filed: Sep. 20, 1984

[51] Int. Cl.[4] ............................................. A61B 17/34
[52] U.S. Cl. ................................. 128/314; 128/329 R
[58] Field of Search .................. 128/329 R, 314, 305, 128/315, 329 A, 330

[56] References Cited

U.S. PATENT DOCUMENTS

| 1,135,465 | 4/1915 | Pollock | 128/329 |
|---|---|---|---|
| 3,030,959 | 4/1962 | Grunert | 128/329 |
| 3,338,239 | 8/1967 | Mausteller | 128/329 R |
| 4,203,446 | 5/1980 | Hofert et al. | 128/329 R |
| 4,375,815 | 3/1983 | Burns | 128/314 |
| 4,416,279 | 11/1983 | Lindner et al. | 128/314 |
| 4,449,529 | 5/1984 | Burns et al. | 128/314 |
| 4,462,405 | 7/1984 | Ehrlich | 128/314 |
| 4,517,978 | 5/1985 | Levin et al. | 128/314 |

FOREIGN PATENT DOCUMENTS

| 188439 | 1/1957 | Fed. Rep. of Germany | 128/314 |
|---|---|---|---|
| 2074453 | 11/1981 | United Kingdom | 128/314 |

Primary Examiner—Gene Mancene
Assistant Examiner—John G. Weiss
Attorney, Agent, or Firm—Robert P. Grindle

[57] ABSTRACT

A disposable lancet assembly is provided, including a housing serving as a lance-holder guide, a lance holder body reciprocable in the housing guide, and a flat-bladed lance mounted in one end of the lance holder body. Included in the invention are integral strategically positioned abutments which serve dual functions providing snap-action drive for the lancet, together with steps for lance movement control. Also included are integral resilient means on the lance holder body providing damping of the lance drive in the puncture direction with automatic withdrawal of the lance into the housing.

9 Claims, 7 Drawing Figures

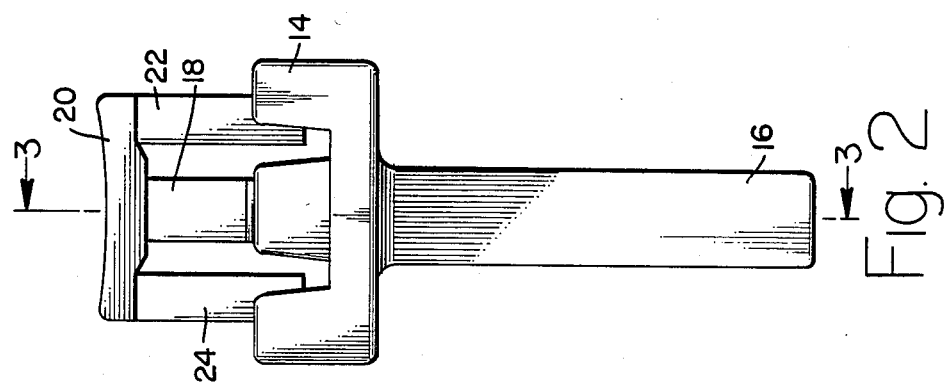
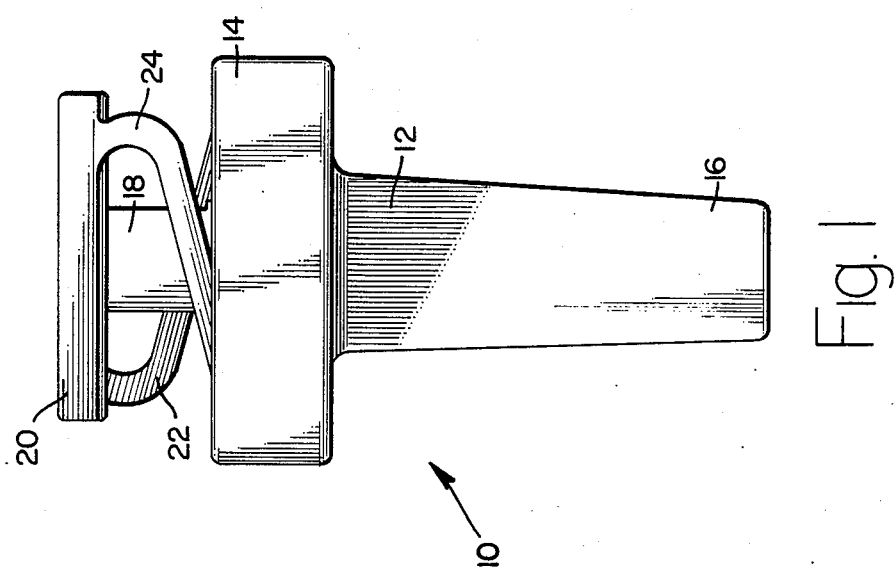

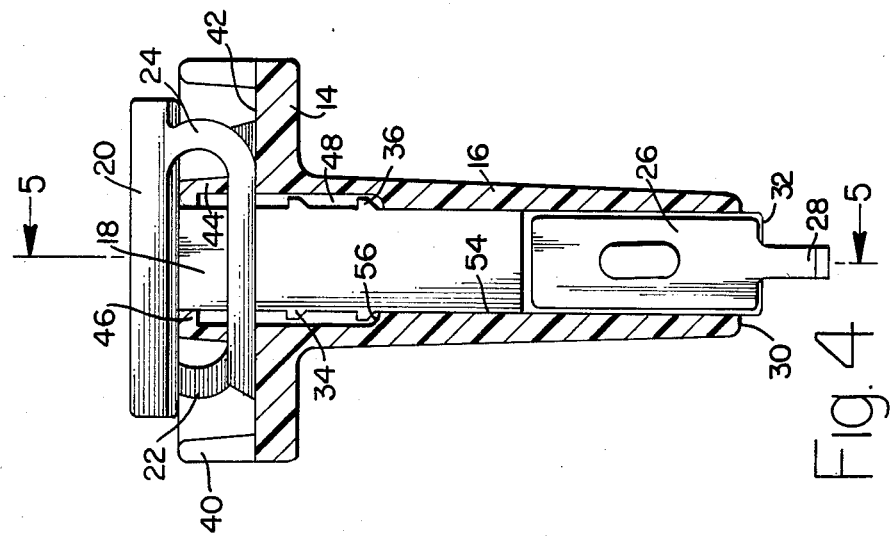
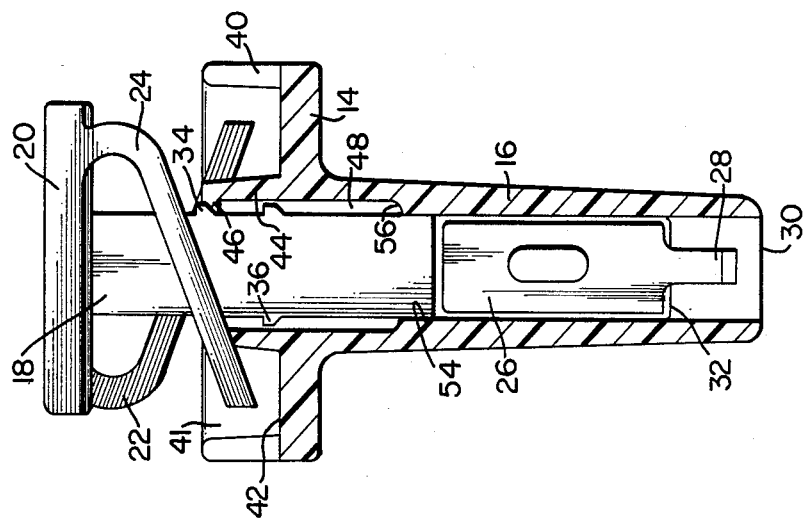

LANCET

BACKGROUND AND DESCRIPTION OF THE INVENTION

The present invention relates to a lancet assembly, and more particularly to such an assembly which provides automatic retractable lancet movement, utilizing resilient means incorporated into the assembly having the dual function of damping the lancet drive movement, together with providing the automatic retraction of the lancet once the puncture is made.

Sharp-pointed lancets have been employed for many years to make a quick puncture or penetration of a patient's skin in order to provide a small outflow of blood. Various tests may be employed with only a small amount of blood so that the blood flowing from a finger prick is normally sufficient to carry out a substantial number of tests. However, due to the sensitive nerve endings in the fingertip area, this procedure sometimes induces a significant amount of pain in the patient, even though the skin puncture produces minimal cutting. Moreover, as will be understood, many people are freightened by the appearance of a blade or skin puncturing apparatus of any kind wherein the cutting portion is available for them to see prior to the puncture. In order to minimize potential pain, as well as reduce apprehension in a patient, it is desirable to make the thrust of the lancet through the patient's skin rapidly and to provide a rapid withdrawl and shielding of the lancet.

Other problems involved with such procedures include contamination by the technician in the procedures involved in taking the blood sample. That is, the patient may have some disease, and if the lancet blade which has carried out the puncture action should prick the skin of a technician subsequent to the initial puncture, the technician and/or nurse and/or doctor involved may be exposed to contamination. Thus, it is important to have automatic retraction of the blade immediately after puncture so that the blade is not exposed for an accidental puncture of someone else's skin.

Spring-loaded lancets of different types and forms have been well known and are typified, for example, by U.S. Pat. Nos. 55,620; 1,135,465; 3,030,959; 4,139,011; 4,203,446; 4,230,118; 4,449,529; and 4,388,925.

U.S. Pat. No. 4,203,446, noted above, is significant in that it teaches the puncture of the skin of a patient with a lancet which is retracted back into the device after piercing the patient's skin. In the patented device, the downward motion of the lancet is initiated by impact of a spring-loaded hammer, and as this motion continues the spring potential decreases. At the time of the impact, the return spring begins to compress and increase potential energy. When the potential energy in the return spring under compression exceeds the potential energy in the driving spring, compression of the return spring ends and decompression begins. This, then reverses the motion of the lancet.

However, impact is necessary to compress the return spring and increase its potential energy rapidly. Without the impact force, the spring forces would approach equilibrium and then there would be no reverse motion in order to retract the lancet out of the patient's skin. Moreover, since spring potential is critical in this patented device, a conical spring is relied upon to overcome recoil due to the surge of the larger return spring. Other problems include, of course, the cost of such an involved assembly. Despite the foregoing inventions, improvements in this field of lancets are still being sought.

With this invention, by contrast, an improved automatic retractable lancet assembly is provided which is relatively simple of construction and easily moldable into two pieces of plastic material. Nevertheless, this simple construction provides, through the utilization of two annular abutments on a lance holder body assembly cooperating with a single annular integral abutment on a lance holder guide, a snap action drive for the lancet to rapidly drive the lancet for the puncture action, with an automatic retraction of the lancet once the puncture has been completed. Moreover, integral with the lance holder body assembly are springs which first provide a damping of the lancet drive, once the cooperating abutments provide the snap action, and, secondly, provide automatic retraction of the lancet. The lance holder portion of the assembly includes a skin compacting front end edge surrounding the lancet blade which automatically engages the skin around the puncture site and moves the skin to provide an accurate skin positioning area at the puncture site, so that the lancet makes a clean puncture rapidly in the area desired.

In accordance with principles of the present invention, the desired functions are achieved by virtue of a very simplified two-piece structure including a lance holder guide comprised of a simple elongated piece of semi-rigid material such as a plastic formed into an elongated body having substantially rectangular passage therethrough. Movable in the passage is an elongated lance holder assembly arranged to have an integral activation handle at one end thereof, and an arrangement for connection of a lance on the opposite end.

The lance holder body assembly includes two spaced integral ridges around the perimeter thereof forming abutments, as well as integral resilient means in the form of leaf springs depending from the handle end of the lance holder body assembly. The abutments cooperate with a single integral abutment around the internal perimeter of the lance holder guide or housing for holding the two parts together prior to use, for providing the snap action in the drive of the lancet to provide the desired puncture, and for providing a stop in both directions of movement of the lance holder. These two molded pieces together with the actual lancet blade provide an appropriate and accurate skin puncture for obtaining and desired quantity of blood for carrying out appropriate tests. Moreover, the arrangement is such that it may be immediately discarded without any danger of contamination by subsequent puncture of those who may handle the used lancet assembly. Nevertheless, even though the structure provides the several desired functions of a modern lancet in use, it is easily manufactured by conventional molding procedures.

Other objects and advantages of this invention will be apparent from the following description, the accompanying drawings and the appended claims.

DESCRIPTION OF THE DRAWINGS

FIG. 1 is a side elevational view of the lancet assembly of the invention;

FIG. 2 is an end view of the lancet assembly of FIG. 1 as viewed from the right-hand end thereof;

FIG. 3 is a partial sectional view of the assembly of FIG. 2 taken along lines 3—3 of FIG. 2;

FIG. 4 is a view similar to that of FIG. 3 but showing the lance holder assembly moved to the skin puncture position;

DETAILED DESCRIPTION OF THE INVENTION

Figure 6:
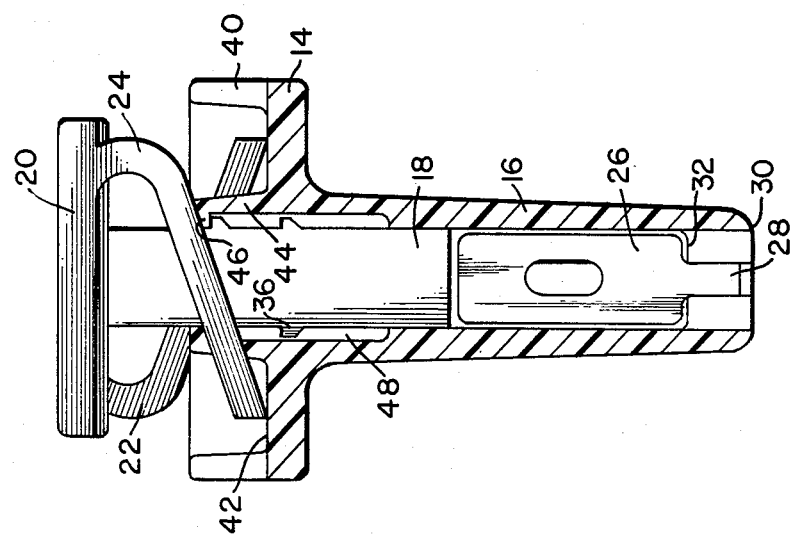
FIG. 6 is a view similar to that of FIGS. 3 and 4 but with the lancet withdrawn after the puncture movement.

Referring to the drawings in which like reference characters refer to like parts throughout the several views thereof, FIG. 1 shows the lancet assembly 10 of the invention from one side, and includes generally rectangular lancet holder guide housing 12 and lance holder body assembly 18 reciprocable therein. Lance holder guide housing 12 includes an elongated lower portion 16 and a wider upper portion 14. Upper portion 14 provides an engaging surface 42 (FIG. 3) for engaging the resilient springs 22, 24 depending from the integral top or handle 20 of lance holder body assembly 18. Top 20 serves as the "push-button" for activating the puncture drive motion of the assembly.

FIG. 2 is a side elevational view of the assembly of FIG. 1 as viewed from the right-hand end thereof. As can be seen from a comparison of FIGS. 1 and 2, the assembly is wider in one dimension than the other providing a generally rectangular assembly. It will be understood by practitioners in the art, however, that lancet assembly 10 can be annular in cross section.

Referring now to FIG. 3, a partial sectional view of the assembly of FIGS. 1 and 2 is shown. As can be seen in FIG. 3, the elongated lance holder body assembly 18 includes lance holder 26 positioned at the opposite end thereof from the integral push-button top 20. Lance holder 26 holds lance blade 28 therein. As can be seen from comparison of FIGS. 3 and 5, blade 28 is a flat wedge-shaped blade for providing a comparatively elongated puncture wound. Lance holder 26 includes a flat end edge 32, which extends beyond the end of the housing 16, through the lower end opening 30 thereof, (as shown in FIG. 4) in order to engage the skin surface and flatten it during the puncture motion.

Housing portion 14 includes an integral upwardly extending wall 40 which defines a space 41 for receiving the lower ends of the resilient springs 22, 24. As can be seen in FIG. 4, the springs in the lower position of lance holder body 18 engage the flat lower surface 42 of the area 41 in the compressed position of springs 22, 24.

Lance holder body 18 includes, as will be seen in FIG. 3, spaced integral abutments 34 36 or ridges around the perimeter thereof. Abutment 34 cooperates with an internally extending integral abutment 46 on housing 16 at the upper end 44 thereof. Abutment 46 defines the upper end of passage 54 in housing 16 through which lance holder body 18 reciprocates. Included in passage 54 is a wider portion 48 into which abutments 34, 36 extend and move, as will be described in more detail below.

Thus, in the initial assembly of the lancet of the invention, lance holder body housing 18 is pushed into the elongated passage 54 in housing 16. In doing so, abutment 36 is pressed past abutment 46. With this arrangement, housing 18 is prevented from slipping out of housing 16 because abutment 36 engages abutment or stop 46, and prevents such disassembly. Thus, in the position shown in FIG. 3, the lancet assembly of the invention is in a position prior to the puncture movement. In this position, lower end of blade 28 is positioned inside opening 30 of housing 16. Also in this position, annular abutment 34 is positioned above (as shown in FIG. 3) cooperating abutment 46.

Thus, the user places end 30 of housing 16 in position on the area to be punctured by the lancet. Thereafter, the user pushes the push-button top 20 and forces abutment 34 past abutment 46. This causes a snap action thrust forward which in turn causes blade 28 to engage and puncture the skin surface. During the course of this movement, the lower end of leaf springs 22, 24 engage surface 42. During a further movement to the position shown in FIG. 4, the springs 22, 24 are further compressed which dampens the forward thrust, once the snap action takes place. For this reason, there is no harsh impact of the lower end 32 of lancet holder 26 during the puncture movement. This damping, therefore, minimizes the effect upon a patient during the entire procedure. Nevertheless, the square flat surface 32 of the lower end of the lance holder 26 serves to spread the area in the vicinity of the puncture so as to make a clean puncture break in the skin.

Figure 5:
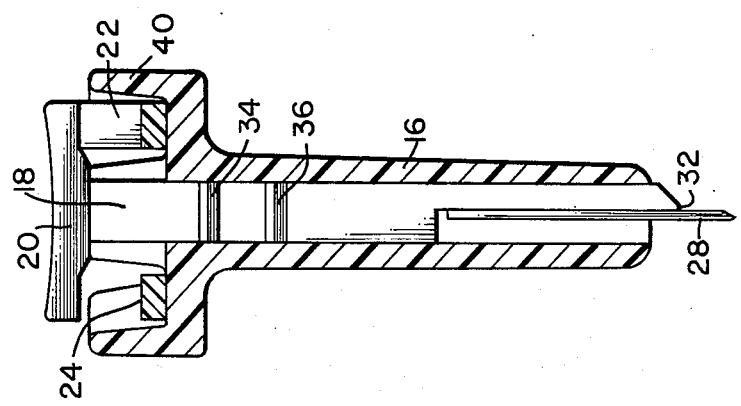
FIG. 5 is a partial longitudinal sectional view taken along lines 5—5 of FIG. 4.

Further movement of body assembly 18 through passage 54 in housing 16 causes lower abutment 36 to engage the ledge 56 defined by the intersection of passage 54 with wider portion 48 thereof, and defining the extent of movement of body assembly 18 in passage 54, which in turn defines and controls the depth of puncture. As shown in FIG. 5, in an end view of the assembly, with lancet blade 28 extending out from opening 30 to its further extent, the flat configuration of blade 28 is clearly shown.

Referring now to FIG. 6, the positioning of the parts of the assembly are shown in the rest position following the puncture movement. That is, springs 22, 24 react from their compressed position as shown in FIG. 4 and move to a relaxed state, as shown in FIG. 6, with the lower ends of springs 22, 24 still engaging surface 42. The reason for this is the interaction of abutment 34 with abutment 46. In the return direction of movement of body assembly 18 in passage 54, abutment 46 serves as a stop for abutment 34. The relaxing of springs 22, 24 and their movement to the position shown in FIG. 6 also causes, automatically, the retraction of blade 28 through opening 30 to a non-exposed position.

Figure 7:
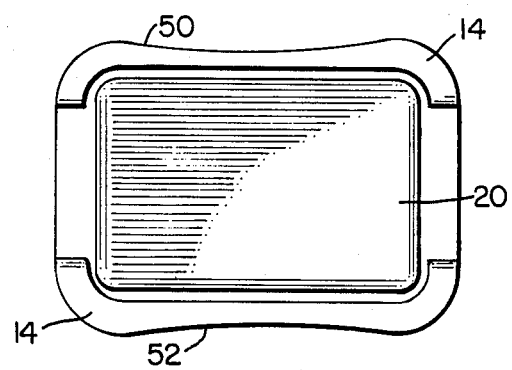
FIG. 7 is a top plan view of the apparatus of FIG. 1.

Referring now to FIG. 7, a further feature of the invention is the configuration of the side panels of housing portion 14 with indentations 50, 52 on either side thereof. These indentations serve to provide finger grip surfaces for the user during a grasping and holding of the assembly for causing the puncture movement.

Thus, as will be appreciated from the above, there is provided in accordance with this invention, a retractable throwaway lancet assembly which is relatively inexpensive and uncomplicated in its construction, but which, nevertheless, provides a structure for imparting a precise drive and puncture with a precise withdrawal of the lancet in one rapid operation of the assembly. The assembly is comprised of two moldable parts which can be mass produced, as will be understood, from a variety of materials including, for example, polyethylene and polypropylene. Materials should be selected which will provide a degree of resiliency for the purpose of providing cooperative movement relative to the cooperating abutments of the assembly, as well as the resiliency required for the leaf springs of the assembly.

While the forms of apparatus herein described constitute preferred embodiments of the invention, it is to be understood that the invention is not limited to these precise forms of apparatus, and that changes may be made therein without departing from the scope of the invention which is defined in the appended claims. For example, whereas one form of spring arrangement is shown for the multi-purpose resiliency required in the arrangement herein, it should be understood that other configurations of integral spring or resilient force may be utilized. Moreover, as stated above, the assembly may be arranged to have a different configuration in cross section. The assembly may be, for example, square or round.

What is claimed is:

1. A lancet assembly comprising,
    (a) an elongated housing;
    (b) a passage extending through said housing with a lancet opening at one end thereof;
    (c) an elongated lancet body reciprocable in said passage;
    (d) a lancet blade positioned in said lancet body at one end thereof;
    (e) handle means on said lancet body at the end thereof opposite said lance blade;
    the improvement characterized by
    (f) a plurality of spaced apart first integral abutment means on said housing and extending into said passage;
    (g) a plurality of spaced apart second integral abutment means on said lancet body for cooperating with said first abutment means;
    (h) integral resilient means on said handle means and extending between said handle means and said housing;
    (i) whereby pushing said handle means causes said body to move through said passage in a first direction making one of said second abutment means to move past one of said first abutment means causing a snap-action in a puncture direction and in turn causing said lancet blade to move through said lance opening;
    (j) said pushing first movement compressing said resilient means and damping said snap-action;
    (k) said pushing first movement stopped by engagement of one of said second abutment means with one of said first abutment means; and
    (l) release of said handle means causing relaxation of said resilient means and movement of said lancet body in said passage in a non-puncture direction until engagement of the other one of said second abutment means with the other one of said first abutment means for maintaining said lance blade, within said housing in a non-contaminating position.

2. The lancet assembly of claim 1, further characterized by
    (a) said spaced apart first integral abutment means comprising
        (1) an abutment extending into said passage around the perimeter thereof and at the end of said passage opposite said lance opening; and
        (2) a ledge formed by the intersection of said passage with an enlarged portion thereof, said ledge extending around the perimeter of said passage; and
    (b) said spaced apart second integral abutment means being two spaced apart abutments integral with said elongated lancet body and extending around the perimeter thereof.

3. The lancet assembly of claim 1, further characterized by
    (a) said resilient means being a pair of resilient leaf springs extending downwardly from said handle means for engaging said housing.

4. The lancet assembly of claim 1, further characterized by
    (a) a lance blade holder integral with said lancet body on the end of said lancet body opposite said handle;
    (b) said lance blade holder for mounting said lance blade; and
    (c) said lance blade holder having a flat skin engaging surface surrounding said lance blade.

5. The lancet assembly of claim 1, further characterized by
    (a) said handle means having finger engaging surfaces thereon.

6. The lancet assembly of claim 1, further characterized by said housing and lancet body being rectangular in cross section.

7. The lancet assembly of claim 1, further characterized by
    (a) said housing and said lancet body comprised of a resilient plastic material.

8. The lancet assembly of claim 3, further characterized by
    (a) said housing comprising an elongated narrower lower portion adjacent said lance opening;
    (b) a wide top portion on the end thereof opposite said lance opening;
    (c) said wide top portion having a flat surface for engagement of said resilient means; and
    (d) an integral upwardly extending wall surrounding said flat surface for retaining said resilient means in the compressed position thereof.

9. The lancet assembly of claim 1, further characterized by
    (a) said lance blade is a flat wedge-shaped blade.

* * * * *